(12) United States Patent  
Richardson et al.

(10) Patent No.: US 9,316,570 B2  
(45) Date of Patent: Apr. 19, 2016

(54) TWO-LAYER TENSION MEASUREMENT SYSTEM FOR COMPRESSION GARMENTS

(71) Applicant: CIRCAID MEDICAL PRODUCTS, INC., San Diego, CA (US)

(72) Inventors: Thomas Richardson, Del Mar, CA (US); Moses A. Lipshaw, Encinitas, CA (US)

(73) Assignee: CIRCAID MEDICAL PRODUCTS, INC., San Diego, CA (US)

( * ) Notice: Subject to any disclaimer, the term of this patent is extended or adjusted under 35 U.S.C. 154(b) by 326 days.

(21) Appl. No.: 13/903,783

(22) Filed: May 28, 2013

(65) Prior Publication Data

US 2013/0319128 A1    Dec. 5, 2013

Related U.S. Application Data

(60) Provisional application No. 61/652,810, filed on May 29, 2012.

(51) Int. Cl.

| | | |
|---|---|---|
| *G01N 3/08* | (2006.01) | |
| *A61H 1/00* | (2006.01) | |
| *A61B 5/103* | (2006.01) | |
| *A61F 13/08* | (2006.01) | |
| *A61B 5/00* | (2006.01) | |

(52) U.S. Cl.
CPC *G01N 3/08* (2013.01); *A61B 5/103* (2013.01); *A61B 5/6804* (2013.01); *A61B 5/6812* (2013.01); *A61F 13/08* (2013.01); *A61H 1/008* (2013.01)

(58) Field of Classification Search
CPC ....... G01N 3/08; A61H 1/008; A61B 5/6812; A61B 5/6804; A61B 5/103; A61F 13/08; A61F 2013/0014

USPC ............ 73/818; 601/151, 33; 602/60, 62, 75, 602/76, 77

See application file for complete search history.

(56) References Cited

U.S. PATENT DOCUMENTS

| | | | |
|---|---|---|---|
| 3,613,679 A | 10/1971 | Bijou | |
| 6,338,723 B1 | 1/2002 | Carpenter et al. | |
| 7,942,838 B2 | 5/2011 | Farrow | |
| 2005/0192524 A1 | 9/2005 | Lipshaw et al. | |
| 2007/0179421 A1* | 8/2007 | Farrow | 602/75 |
| 2009/0247980 A1 | 10/2009 | Aiken | |
| 2010/0312160 A1 | 12/2010 | Creighton et al. | |
| 2012/0179084 A1* | 7/2012 | Lipshaw et al. | 602/75 |

OTHER PUBLICATIONS

International Search Report, Oct. 13, 2013.

* cited by examiner

*Primary Examiner* — Lisa Caputo  
*Assistant Examiner* — Philip Cotey  
(74) *Attorney, Agent, or Firm* — Troutman Sanders LLP

(57) ABSTRACT

A two layer compression garment measuring system that displays a pressure indicia when the garment is stretched, wherein the pressure indicia is displayed by moving from a position under an opaque layer of material (at low or no pressure) to a position under a window or transparent or translucent layer of material (at higher pressure). When the indicia can be seen by an observer through the window or transparent or translucent layer, then the higher pressure has been reached. The viewed indicia optionally displays the pressure level. In various optional designs, the location of attachment between the two spaced-apart locations is adjustable, or the length of the upper layer is adjustable such that the attachment location can be aligned with the indicia. A design having a free ended upper layer is also included.

20 Claims, 16 Drawing Sheets

TWO-LAYER TENSION MEASUREMENT SYSTEM FOR COMPRESSION GARMENTS

RELATED APPLICATION

The present application claims priority to U.S. Provisional Patent Application 61/652,810, entitled "Graduated Compression For The Treatment Of Circulatory Disorders Such As Lymphedema and Venus Disease", filed May 29, 2012, the entire disclosure of which is incorporated herein by reference in its entirety for all purposes.

TECHNICAL FIELD

The present invention relates to therapeutic compression garments and to systems for measuring the compression forces in these garments.

BACKGROUND OF THE INVENTION

Compression therapy is a common treatment for lymphedema and venous disease. Numerous compression garments exist to apply therapeutic pressures to a patient's limb. These garments wrap around the arm or leg of a patient and apply a compressive force to the affected limb. As these garments are stretched around the limb, they apply the compressive force. According to La Place's Law, the compression applied is a function of the tension, limb circumference and width of the garment/band. The farther that these garments are stretched (and the stiffer the material they are made of), the greater the compressive force applied to the limb. As a result, the compression level relates directly to the amount of stretch in the material.

Research has shown that certain compression levels are optimal to treat different circulatory ailments. Because there is a proven benefit to applying specific known levels of compression to the limb, there is a need for devices that can accurately measure the level of compression being applied. In the past, such compression measuring devices have included measurement cards (which measure the increasing distance between indicia on the garment as the garment is stretched). An example of this system is found in U.S. Pat. No. 6,338,723 owned by Circaid Medical of San Diego, Calif. Other measurement systems are found in U.S. Pat. Nos. 3,613,679 and 7,942,838. However, a simpler and more easy to use system is desirable.

Specifically, what is desired is a compression garment having a built-in system that readily shows the compression level to the patient. Such a new system should be convenient to use, accurate, and not require a separate calibration tool. As will be explained below, the present invention provides such a system.

SUMMARY OF THE INVENTION

The present invention provides a compression garment having a built-in measurement system. This measurement system may either be built into the bands of a wrap-around garment, or be built into the side of a tubular garment.

In one preferred aspect, the present invention provides a two-layer compression measurement system, comprising:
(a) a stretchable base layer having indicia thereon; and
(b) a stretchable upper layer positioned on top of the stretchable base layer,
  (i) wherein the stretchable upper layer comprises a first portion and a second portion attached end-to-end, the first and second portions having different stiffnesses, and
  (ii) wherein the stretchable upper layer is attached to the stretchable base layer at two spaced-apart locations such that the first portion of the upper layer is attached to the base layer at a first location and the second portion of the base layer is attached to the base layer at a second location, and
  (iii) wherein the first portion of the upper layer permits viewing therethrough such that a user can see the indicia on the base layer.

It is to be understood that the word "indicia" as used herein in both the specification and claims also refers to a single indicium marking. Thus, the claims reciting "indicia" also cover embodiments of the invention having only one indicium.

In this aspect of the invention, the first portion of the upper layer has a window passing through it, and the user views the indicia through the window. In another aspect of the invention, the second portion of the upper layer is transparent or translucent and the first portion of the upper layer is opaque, and the user views the indicia through the transparent or translucent second portion.

As the user stretches the garment, the indicia on the base layer moves into a position underneath the window or transparent/translucent layer. This is because the base and upper layers stretch together, but the upper layer is made of two portions of different stiffness. As a result, one of the portions will stretch more than the other. This results in what appears to the user as a relative movement of the window or transparent/translucent layer with respect to the indicia on the base layer underneath that stretches less.

In other preferred aspects, the present invention provides a two-layer compression measurement system comprising base and upper layers wherein the upper layer is attached to the stretchable base layer at two spaced-apart locations, and the location of attachment at one of the two spaced-apart locations is adjustable such that the location of attachment can be aligned with the indicia on the stretchable base layer.

In yet other aspects, the present invention provides a two-layer compression measurement system comprising base and upper layers wherein the length of the upper layer is adjustable such that the location of attachment can be aligned with the indicia on the upper layer.

In yet other aspects, the present invention provides a two-layer compression measurement system wherein the indicia on the stretchable base layer are disposed under the free end of the upper layer and are not visible to a user before the measurement system has been stretched, but are pulled out from under the free end of the upper layer and are therefore visible to the user after the measurement system has been stretched.

In yet other aspects, the indicia on the stretchable base layer protrude from the side edges of the upper layer, such that the indicia appear to move with respect to the upper layer as the garment is stretched.

In optional preferred aspects, the indicia on the base or upper layer can be a series of indicia corresponding to different tension levels. Optionally, these indicia may display the tension levels as numerical values (e.g.: 20 mmHg, 30 mmHg, etc.), or they may be colors corresponding to different stretch levels (e.g.: GREEN for lower acceptable pressures and RED for higher, unsafe compression levels, etc.).

DETAILED DESCRIPTION OF THE DRAWINGS

Figure 1A:
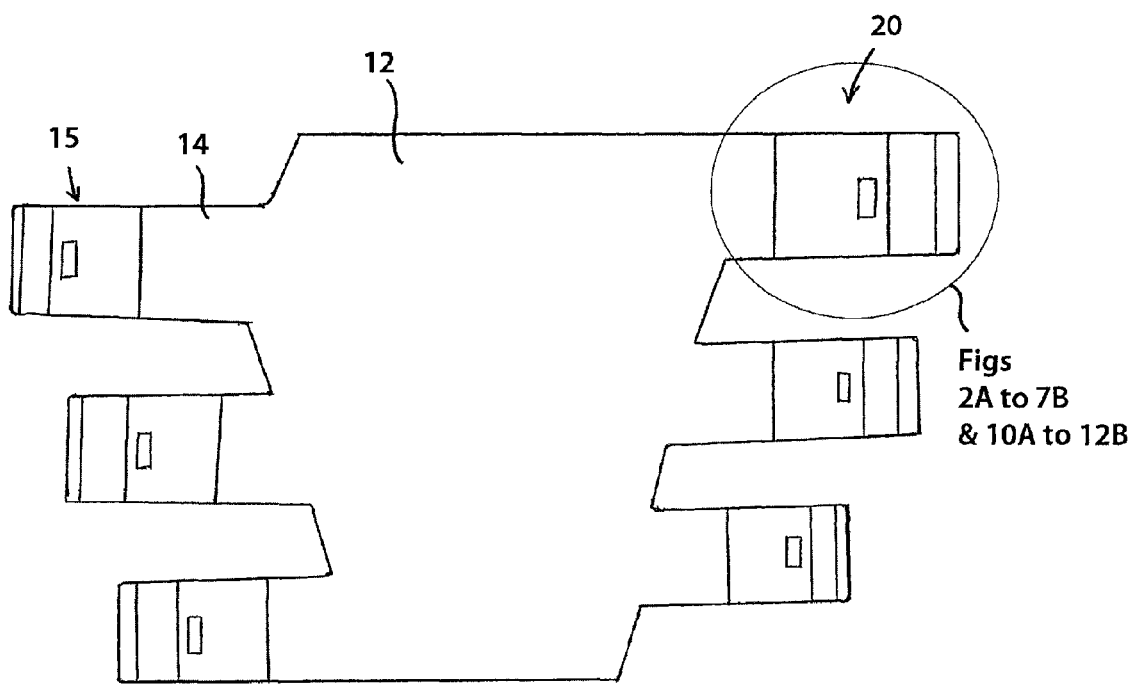
FIG. 1A is a top plan view of a wraparound compression garment incorporating the present measurement system into its bands prior to use.
Figure 1B:
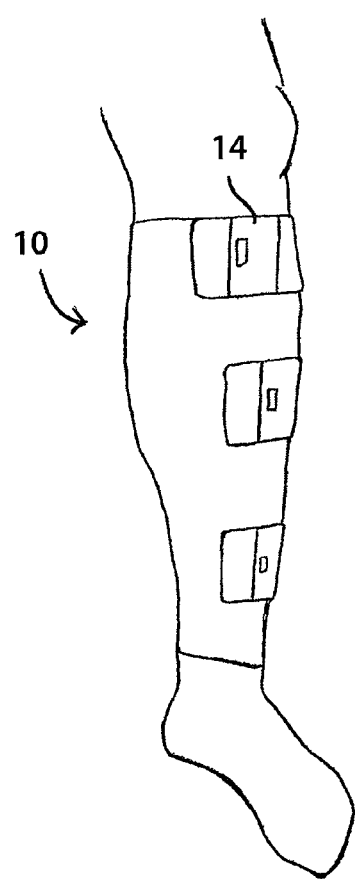
FIG. 1B is a perspective view of the garment of FIG. 1A after it has been wrapped around the limb of a patient.

FIG. 1A is a top plan view of a compression garment incorporating the present measurement system into its bands. Specifically, garment 10 has a main body 12 with a plurality of bands 14 extending therefrom. Garment 10 is wrapped around the limb of a patient (as seen in FIG. 1B) with juxtaposed interlocking bands 14 preferably comprising Velcro® hook and loop fasteners. Specifically, garment 10 is wrapped around the patient's limb with the Velcro® hook and loop fasteners 15 on the underside (not shown) of bands 14 being attached to Velcro® hook and loop surfaces on the front of the garment.

FIGS. 2 to 7B and 10A to 13B are all close up views of the present measurement device installed in one or more bands 14 of the garment as shown in FIG. 1. It is to be understood, however, that the present measurement device can be incorporated in any suitable compression system or garment.

Figure 2:
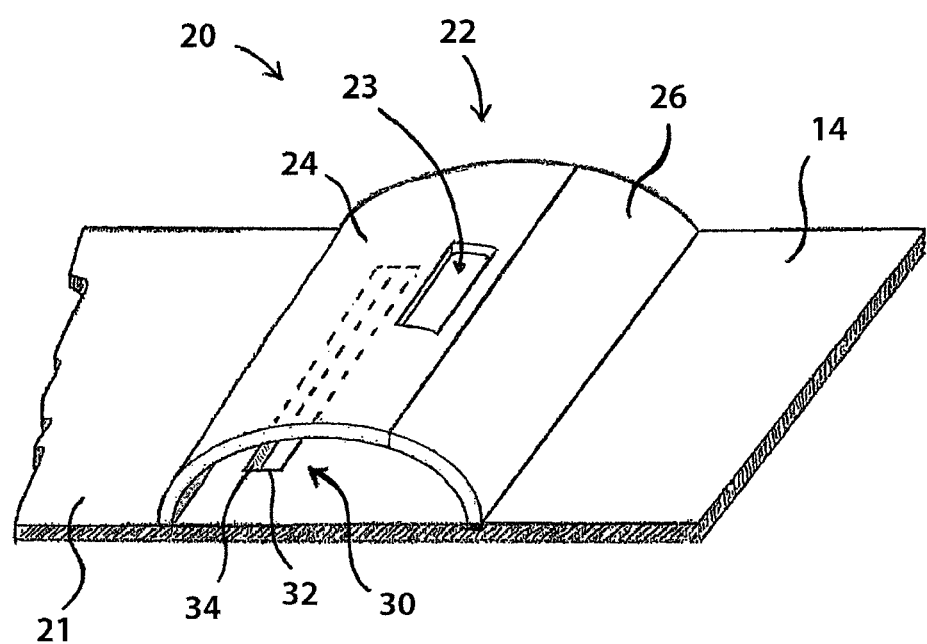
FIG. 2 is a close up perspective view of the measurement system in one of the bands prior to any stretching of the band.

FIG. 2 is a perspective view of a first embodiment of the invention, as follows. Compression measurement system 20 is a two-layer measurement system. Measurement system 20 comprises: a stretchable base layer 21 having indicia 30 thereon; and a stretchable upper layer 22 positioned on top of the stretchable base layer. Importantly, stretchable upper layer 22 comprises a first portion 24 and a second portion 26 joined end-to-end. Importantly as well, first portion 24 and second portion 26 have different stiffnesses. (For example, first portion 24 may be inelastic and second portion 26 may be elastic). One end of first portion 24 is attached (e.g.: sewn) to base layer 21 and one end of second portion 26 is also attached (e.g.: sewn) to base layer 21, as illustrated. The other ends of first and second portions 24 and 26 are also attached (e.g.: sewn) together, as also illustrated.

It is to be understood that either or both of the two layers in the present invention may in turn be made of two, three or more layers or sections connected together, and therefore any references in the specification and claims to two layers refer to at least two layers, each made of one, two, three or more layers or sections connected together.

Indicia 30 may be printed, painted, glued or sewn onto or otherwise attached to the upper surface of base layer 21. In one preferred embodiment, indicia 30 comprise a green marking 32 and a red marking 34. In other preferred embodiments, the indicia may comprise a tension force scale calibrated to display different tension levels. In operation, indicia 30 can be seen by a user through window 23 in first portion 24 of top layer 22.

Figure 3A:
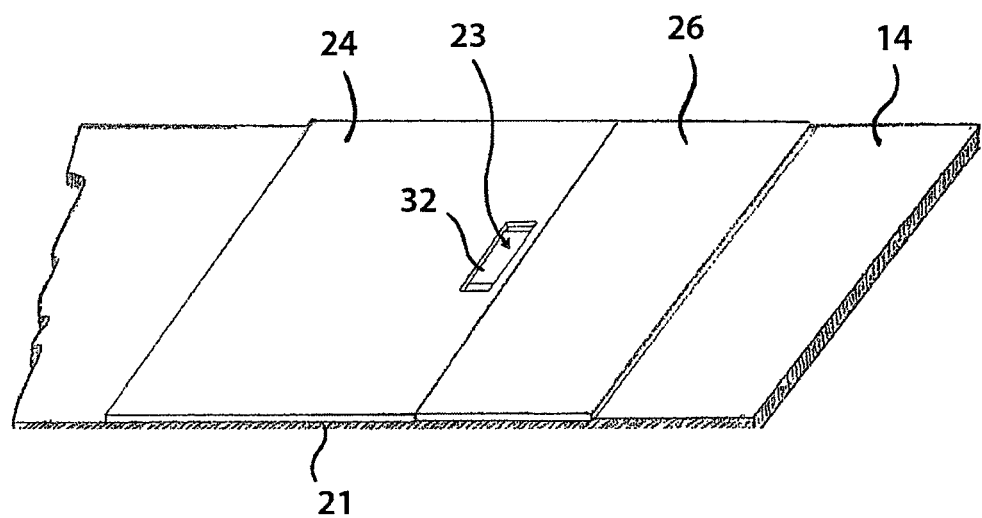
FIG. 3A is a perspective view of the measurement system of FIG. 2 with light tension applied to the band.
Figure 3B:
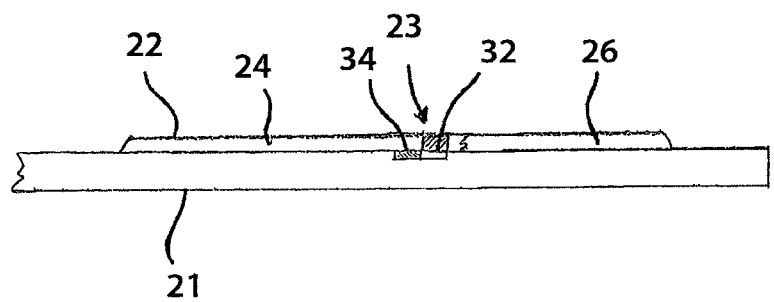
FIG. 3B is a sectional side elevation view corresponding to FIG. 3A.

FIGS. 3A and 3B show light tension applied to measurement system 20. At this time, the Green indicia 32 is viewable through window 23.

Figure 4A:
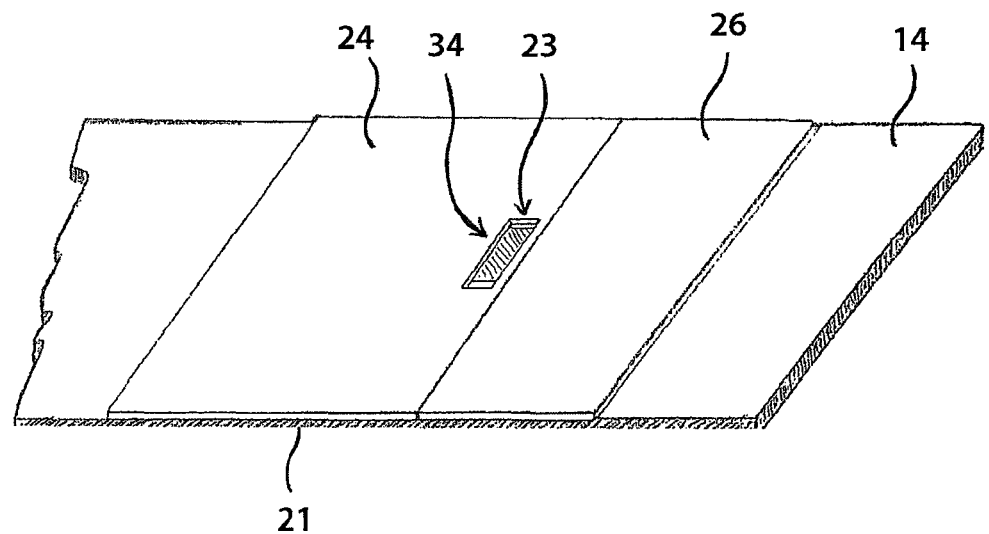
FIG. 4A is a perspective view of the measurement system of FIG. 2 with greater tension applied to the band.
Figure 4B:
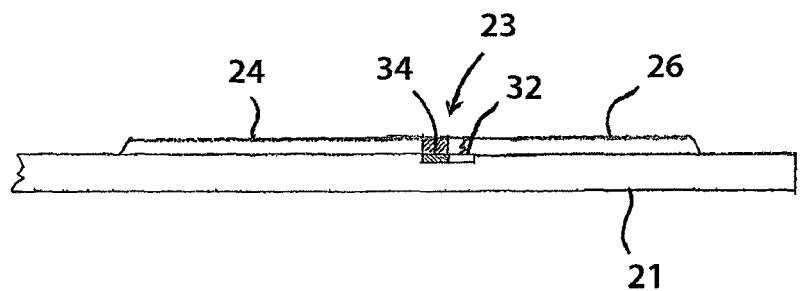
FIG. 4B is a sectional side elevation view corresponding to FIG. 4A.

Next, a greater tension is applied as seen in FIGS. 4A and 4B. Portion 24 is stiffer than portion 26. As a result, first portion 24 will stretch less than second portion 26 when the two portions are stretched together as a unit. This will appear to cause window 23 to move with respect to base layer 21 therebelow. Therefore, as can be seen in FIGS. 4A and 4B, when the higher level of tension is applied to band 14, Red marking 34 will instead be seen through window 23.

Therefore, as a result of varying the tension in band 14, different indicia will be seen through window 23 at different tension levels. This provides a novel, easy to use measurement system for a user. For example, when the user sees the Green indicia 32 (s)he knows the tension is at a safe or preferred level. Conversely, when (s)he sees a Red indicia 34 through window 23, (s)he knows that the tension is at an excessively high or unsafe level.

Indicia 30 can be as simple as two calibrated markings 32 and 34 labelling acceptable and unacceptable tension levels. It is to be understood, however, that indicia 30 may instead comprise a series of graduated markings with "high", "medium" and "low" tension levels. Many other possibilities are also contemplated within the scope of the present invention. For example, the placement of the indicia can be calibrated such that the indicia display numbers corresponding to known compression levels. (For example, the indicia viewable through the window 23 can be numbers stating the tension level in the garment—e.g.: 20 mm Hg, 30 mmHg, 40 mmHg, etc.).

Figure 5:
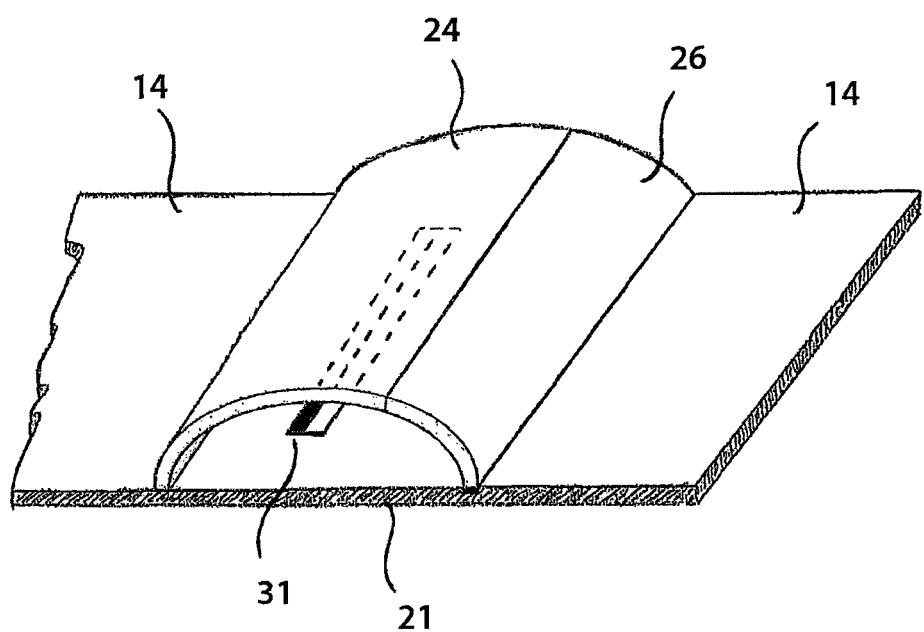
FIG. 5 is a perspective view of a second embodiment of the measurement system in the band.
Figure 6A:
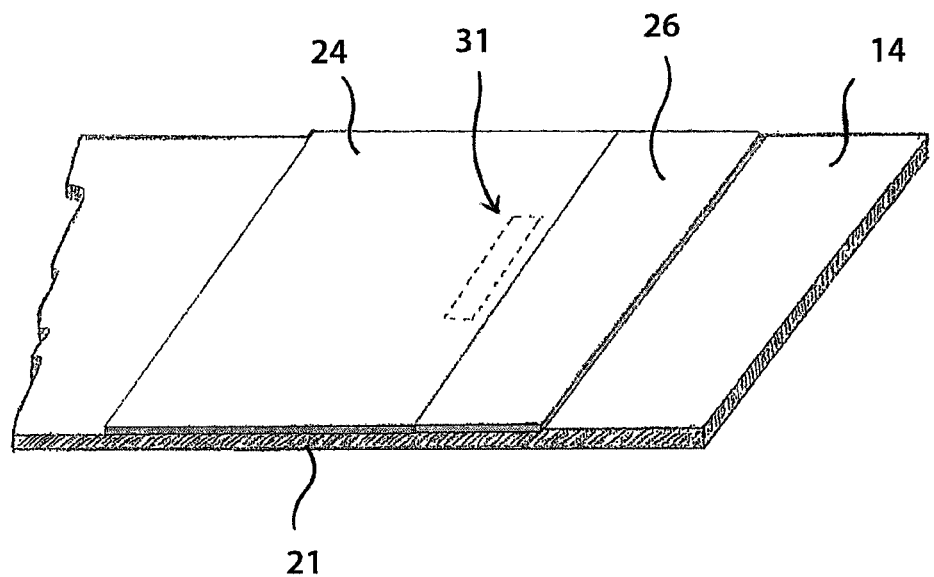
FIG. 6A is a perspective view of the measurement system of FIG. 5 with light tension applied to the band.
Figure 6B:
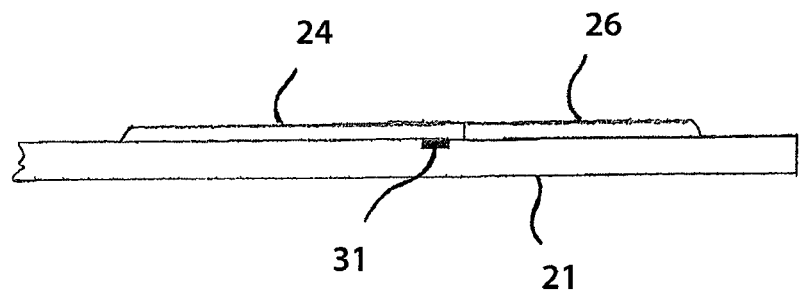
FIG. 6B is a sectional side elevation view corresponding to FIG. 6A.
Figure 7A:
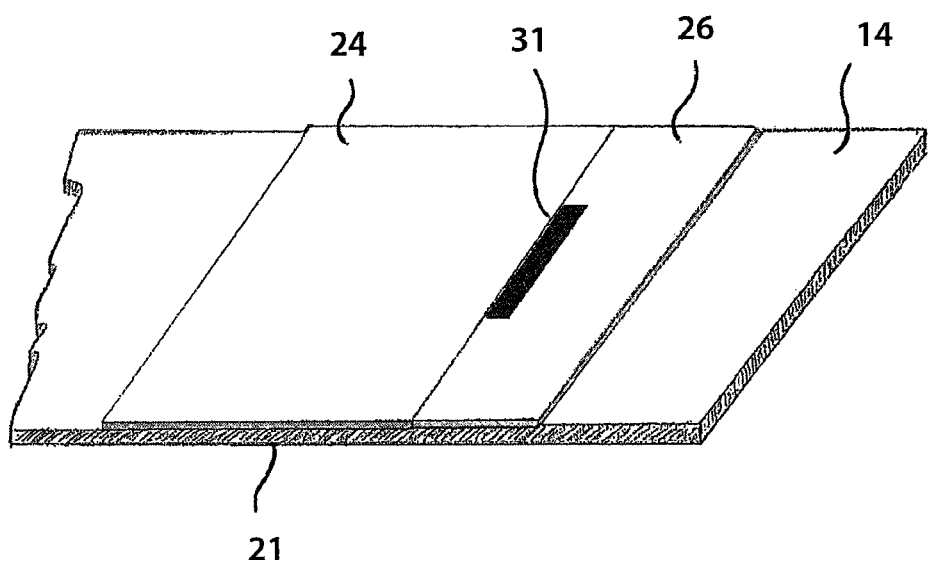
FIG. 7A is a perspective view of the measurement system of FIG. 5 with greater tension applied to the band.
Figure 7B:
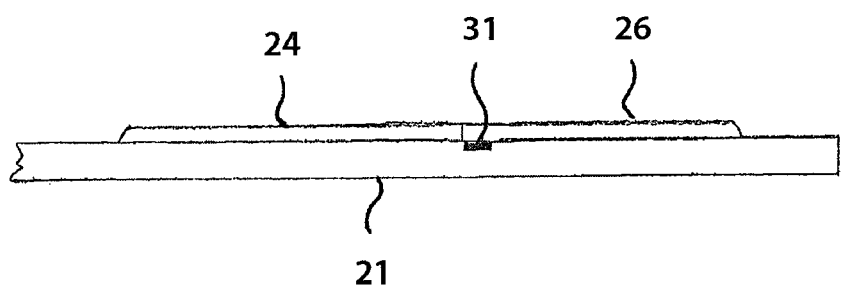
FIG. 7B is a sectional side elevation view corresponding to FIG. 7A.

FIG. 5 is a perspective view of a second embodiment of the measurement system in the band. This embodiment is quite similar in operation to the first embodiment described above. The difference is that this second embodiment does not have window 23. Instead, second portion 26 is made of a transparent or translucent material such that indicia 30 is viewable therethrough. In this embodiment, indicia 30 can simply comprise a Red line 31 extending across base layer 22. FIGS. 6A and 6B show the band under very light tension. At this time, red line indicia 31 is disposed underneath of opaque first portion 24. As greater tension is applied to band 14, it reaches the position illustrated in FIGS. 7A and 7B where red line indicia 31 is now disposed underneath of the transparent or translucent second portion 26. Thus, red line indicia 31 provides an easy to use measurement system. Simply put, whenever the user sees red line indicia 31 (s)he knows that the garment has been overstretched.

It is to be understood that the use of a red line indicia 31 is not the only configuration of indicia suitable for use with this second embodiment of the invention. For example, a series of different indicia (such as a graduated scale) could instead be used. For example, parallel red, yellow and green lines could be used to indicate "low", "medium" and "high" tensions. In such a system, the user would see only a green line at low pressures, parallel green and yellow lines at medium pressures and parallel green, yellow and red lines at high pressures. Moreover, instead of colored lines, actual compression levels could be the indicia used. Thus, the user would see "20 mmHg" or "30 mmHg", etc. at these different tension levels.

Figure 8A:
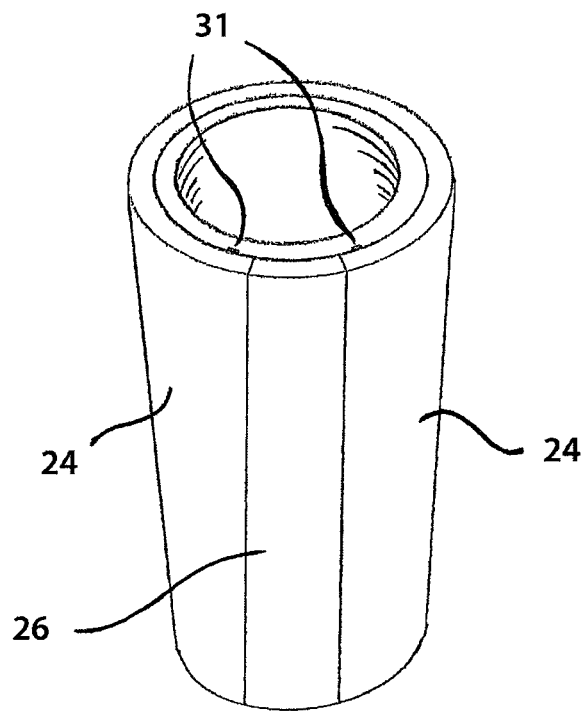
FIG. 8A is a perspective view of a third embodiment of the present invention disposed in a tubular compression garment.
Figure 8B:
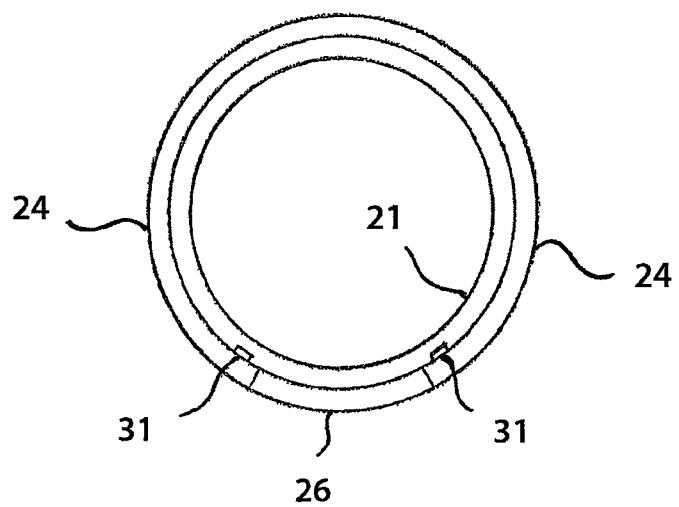
FIG. 8B is a sectional top plan view corresponding to FIG. 8A.
Figure 9A:
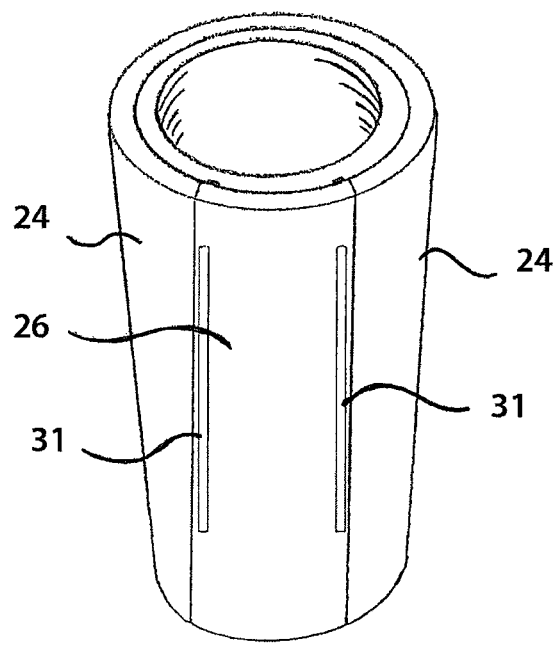
FIG. 9A is a perspective view of the garment of FIG. 8A after the garment has been stretched outwardly to fit around the limb of a patient.
Figure 9B:
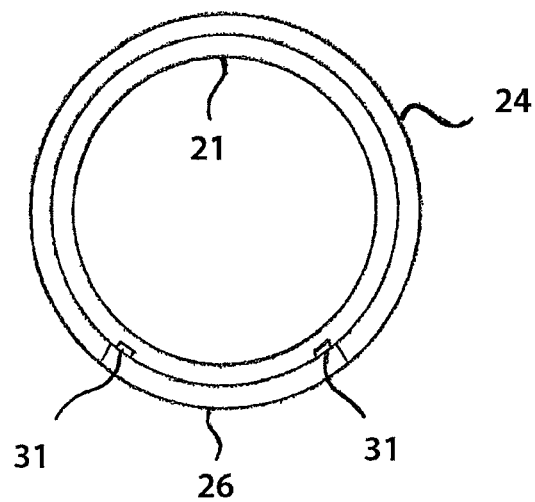
FIG. 9B is a sectional top plan view corresponding to FIG. 9A.

A third embodiment of the present invention is using the measurement system in a tubular pull-on compression garment. This is illustrated in FIGS. 8 to 9B as follows. FIGS. 8A and 8B show the garment prior to it being stretched to fit over the limb of a patient. At this stage, the pair of indicia 31 is hidden under opaque first layer 24. Next, as illustrated in FIGS. 9A and 9B, when the garment has been stretched to fit around the limb of a patient, indicia 31 becomes visible through the transparent second layer 26. As a result, the user knows that they have reached the maximum "red line" limit of use, and to now stretch the garment beyond this limit.

It is to be understood that either of the transparent/translucent (FIGS. 5 to 7B) or the window (FIGS. 2 to 4B) embodiments could be used with the tubular compression garment shown in FIGS. 8A to 9B.

It is also to be understood that the indicia used with the tubular embodiment of the invention can also be a graduated scale or even specific tension levels lines (e.g.: "20 mmHg", "30 mm Hg", etc.) as was described above with relation to the other embodiments of the invention.

Figure 10A:
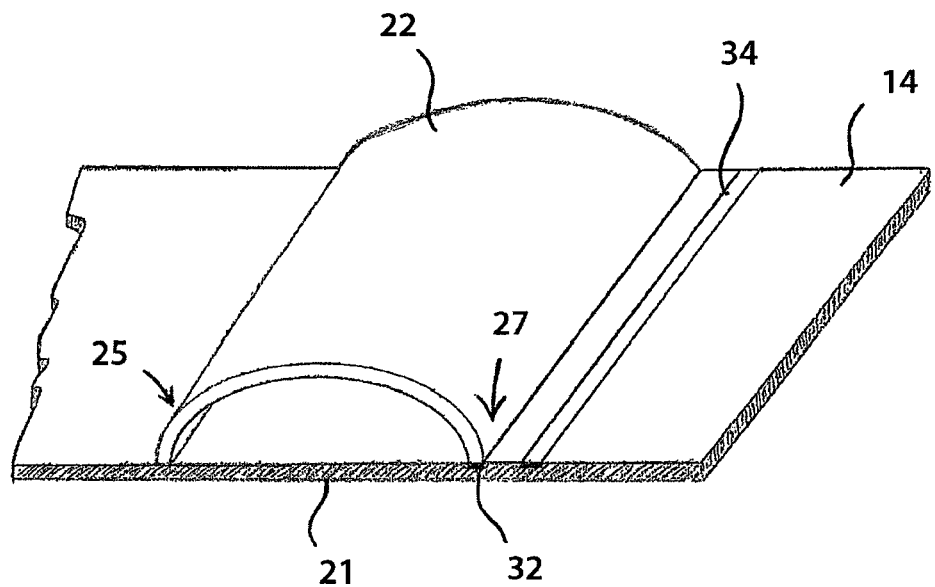
FIG. 10A is a perspective view of a fourth embodiment of the measurement system disposed in the band prior to tension being applied to the band.
Figure 10B:
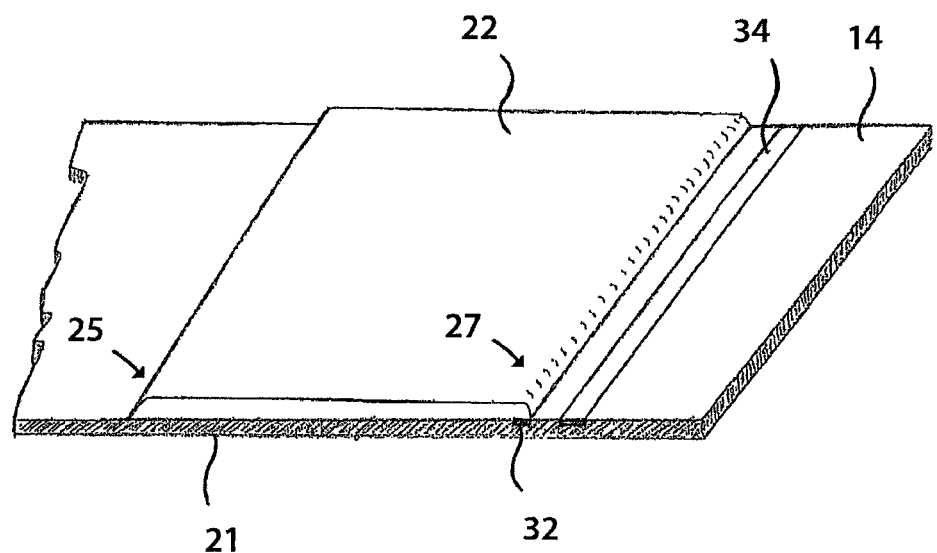
FIG. 10B is a perspective view corresponding to FIG. 10A after tension has been applied to the band.

A fourth embodiment of the invention is seen in FIGS. 10A and 10B. In this embodiment, stretchable base layer 21 has indicia 32 and 34 thereon. Upper layer 22 is positioned on top of the stretchable base layer 21. Upper layer 22 may be inelastic, but need not be so. (For example, being inelastic may be an advantage at maximum compression levels, However, having some elasticity may be an advantage, to allow users to apply more compression if needed. Upper layer 22 is fixed (e.g.: sewn or glued, etc.) to stretchable base layer 21 along location 25, but is releasably attached (e:g: by Velcro® hook and loop fasteners) along location 27 (or is glued or sewn along location 27). Thus, location 27 is adjustable depending upon the placement of the hook and loop fasteners. Therefore, should the user want a looser fit, the user attaches the free end of upper layer 22 such that it is aligned with indicia 32. When the band 14 is then stretched (to the position of FIG. 10B), upper layer 22 will lay flat with its free end fastened along indicia 32. The inelastic nature of upper layer 22 will prevent further stretching of the stretchable base layer 21. However, should the user want a greater compression in the band, the user will instead align the free end of upper layer with indicia 34 (i.e.: move location 27 to cover indicia 34). As a result, upper layer will not be able to stretch as far under tension. Indicia 32 and 34 will thereby correspond to different pre-determined compression levels.

Figure 10C:
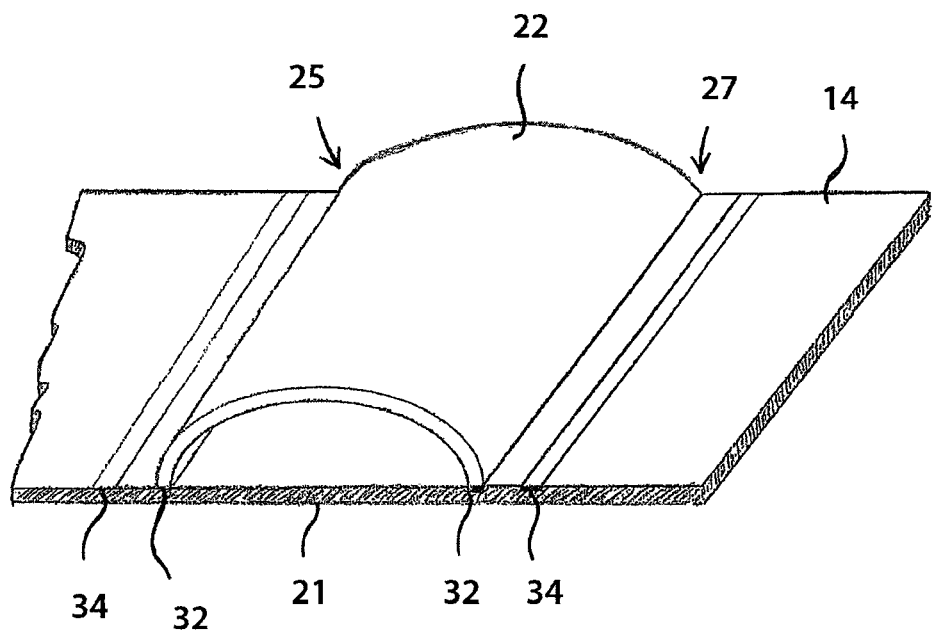
FIG. 10C is similar to FIG. 10A, however both ends of the upper layer are positionable on the stretchable base layer.
Figure 10D:
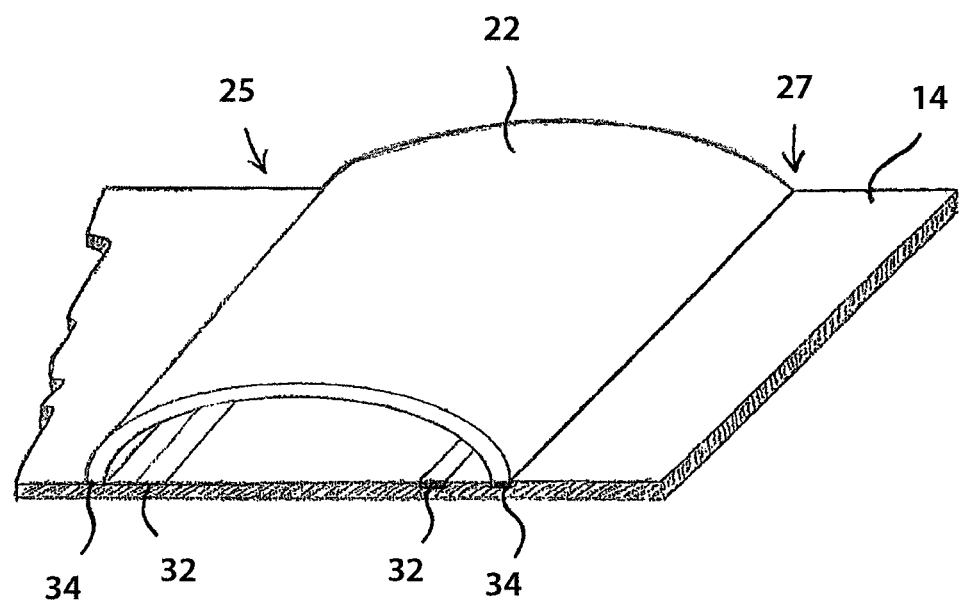
FIG. 10D is similar to FIG. 10C, but is more resistant to stretching due to the placement of the upper layer.

FIGS. 10C and 10D show a similar embodiment, however, the upper layer 22 is releasably attached (e:g: by Velcro® hook and loop fasteners) along both of locations 25 and 27. IE: it is not sewn or glued along location 25. As a result, the user may attach both edges of upper layer 22 at locations 25 and 27 corresponding to indicia 32 as shown in FIG. 10C. However, should the user want a tighter fit, (s)he would instead attach both edges of upper layer 22 at locations 25 and 27 corresponding to indicia 34 as shown in FIG. 10D.

Figure 11A:
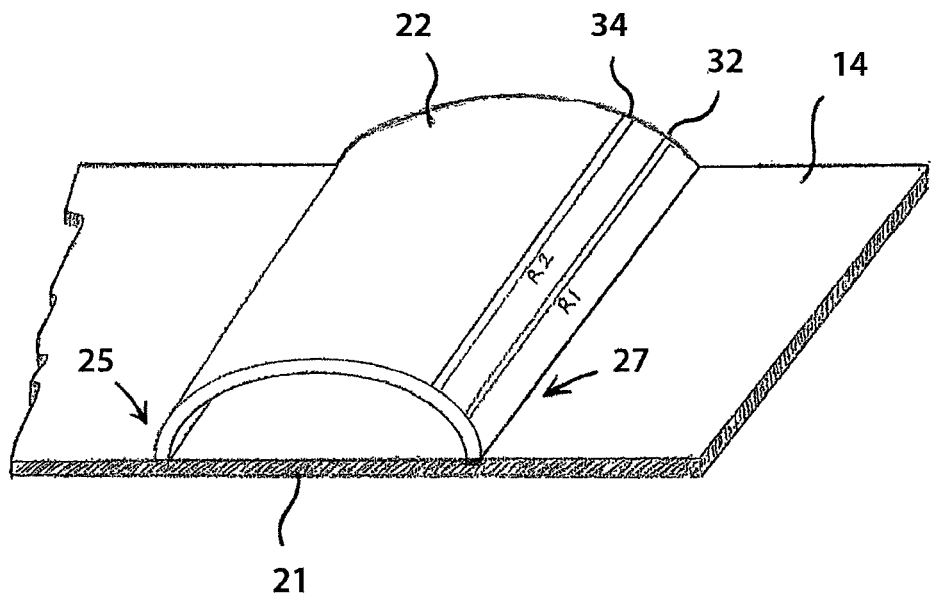
FIG. 11A is a perspective view of a fifth embodiment of the measurement system disposed in the band prior to tension being applied to the band.
Figure 11B:
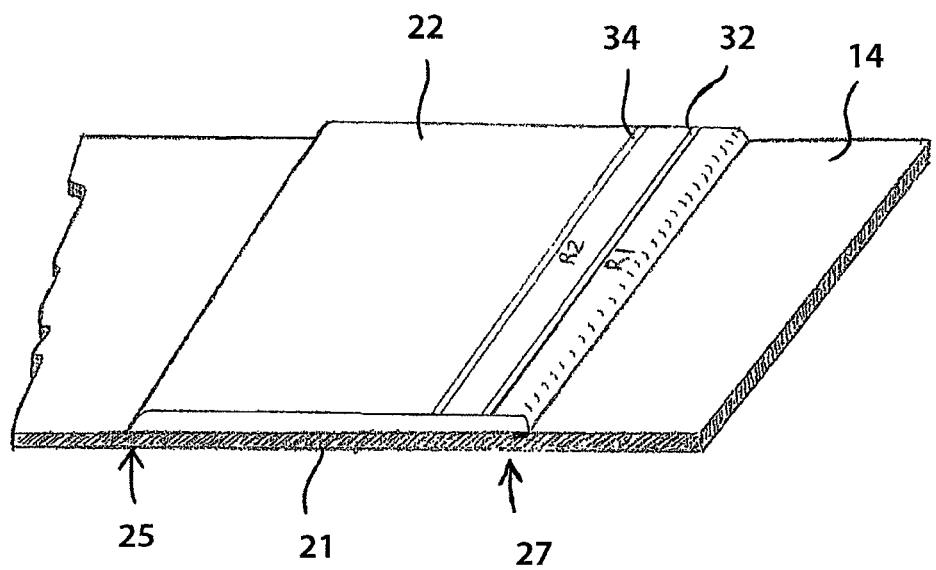
FIG. 11B is a perspective view corresponding to FIG. 11A after tension has been applied to the band.

A fifth embodiment of the invention is seen in FIGS. 11A and 11B. In this embodiment, the upper layer has indicia 32 and 34 thereon. Upper layer 22 is positioned on top of the stretchable base layer 21. Upper layer 22 is preferably inelastic. Upper layer 22 is fixed (e.g.: sewn or glued, etc.) to stretchable base layer 21 along location 25, but is releasably attached (e:g: by Velcro® hook and loop fasteners) along location 27 at its free end. In contrast with the embodiment of FIGS. 10A and 10B, the location 27 in FIGS. 11A and 11B does not move. Instead, the user cuts the free end of upper layer 22. Should the user want a looser fit, the user cuts and removes portion R1, thereby placing the free end of upper portion 22 (which will have indicia 32 running therealong) at location 27. However, should the user want a greater compression in the band, the user will instead cut away portions R1 and R2, thereby placing the free end of upper portion 22 (which will now have indicia 34 running therealong) at location 27. Indicia 32 and 34 will thereby correspond to different pre-determined compression levels.

Figure 12A:
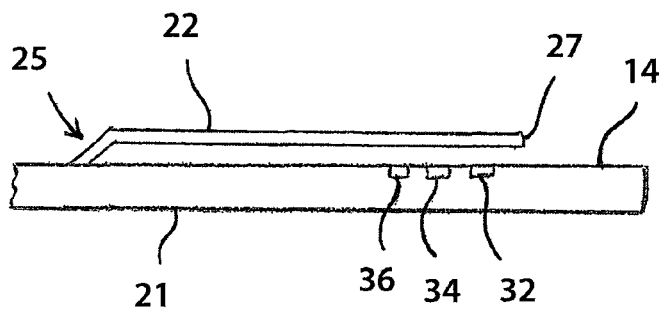
FIG. 12A is a perspective view of a sixth embodiment of the measurement system disposed in the band prior to tension being applied to the band.
Figure 12B:
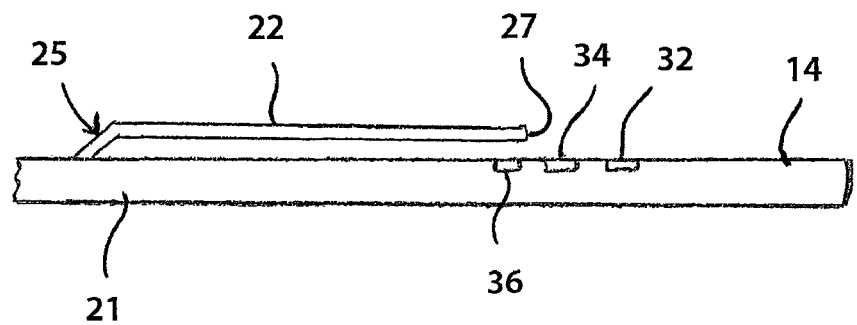
FIG. 12B is a perspective view corresponding to FIG. 12A after tension has been applied to the band.

A sixth embodiment of the invention is seen in FIGS. 12A and 12B. In this embodiment, the stretchable base layer 22 has indicia 32, 34 and 36 thereon. The upper layer 22 is positioned on top of stretchable base layer 22, having one fixed end 25 that is attached to the stretchable base layer, and one free end 27 that is not attached to the stretchable base layer. FIG. 12A shows the system with no tension applied. At this time, all of the indicia 32, 34 and 36 are covered by one free end 27 and are not visible to the user. Next, tension is applied such that indicia 32 and 34 on stretchable base layer 22 are pulled out from under free end 27 of upper layer 21. At this time, indicia 32 and 34 are visible to the user. The placement of indicia 32, 34 and 36 is preferably marked and calibrated such that the visibility of indicia 32 corresponds to a first compression level (e.g.: 20 mmHG); the visibility of both indicia 32 and 34 corresponds to a second compression level (e.g.: 30 mmHG); the visibility of all three indicia 32, 34 and 36 corresponds to a third compression level (e.g.: 40 mmHG).

Figure 13A:
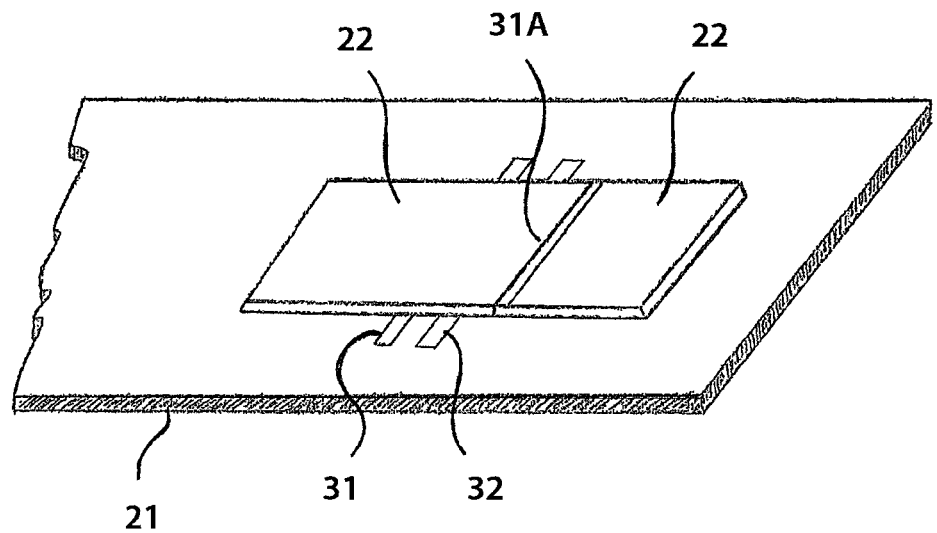
FIG. 13A is a perspective view of a seventh embodiment of the measurement system in which the indicia on the stretchable base layer protrude out from under the side edges of the upper layer prior to tension being applied.
Figure 13B:
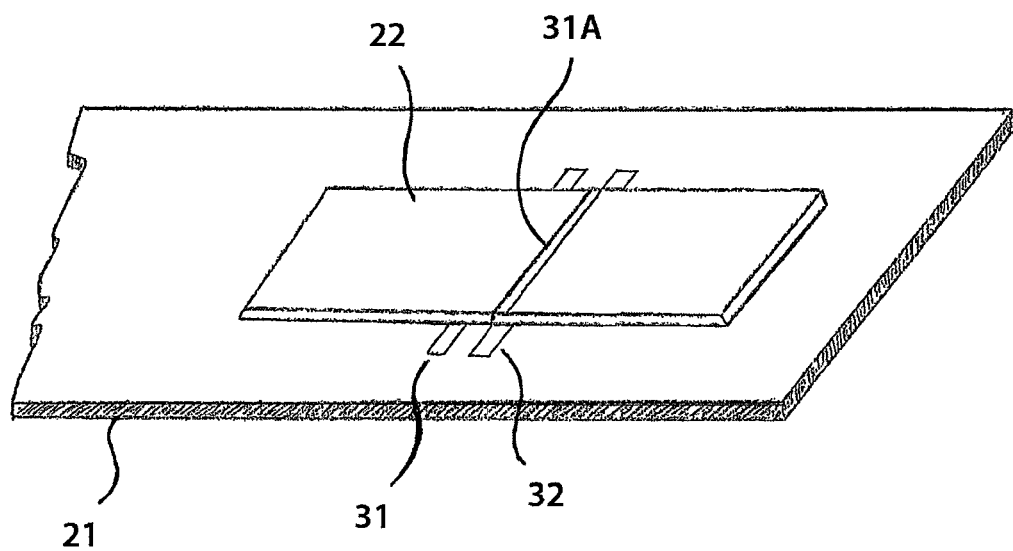
FIG. 13B is a perspective view corresponding to FIG. 13A, after tension has been applied showing the movement of the indicia with respect to the upper layer.

A seventh embodiment of the invention is seen in FIGS. 13A and 13B. In this embodiment, the stretchable base layer 21 has two parallel indicia lines 31 and 32. Upper layer 22 is opaque and has an indicia line 31A running thereacross. Prior to any tension being applied (as seen in FIG. 13A), neither of the indicia lines 31 or 32 will align with indicia line 31A. Later, after tension is applied to band 14, indicia 32 (on base layer 21) and indicia 31A (on upper layer 22) will align with one another (as seen in FIG. 13B). Should an even greater tension be applied, indicia 31 on base layer 21 will align with indicia 31A on upper layer 22.

Figure 14A:
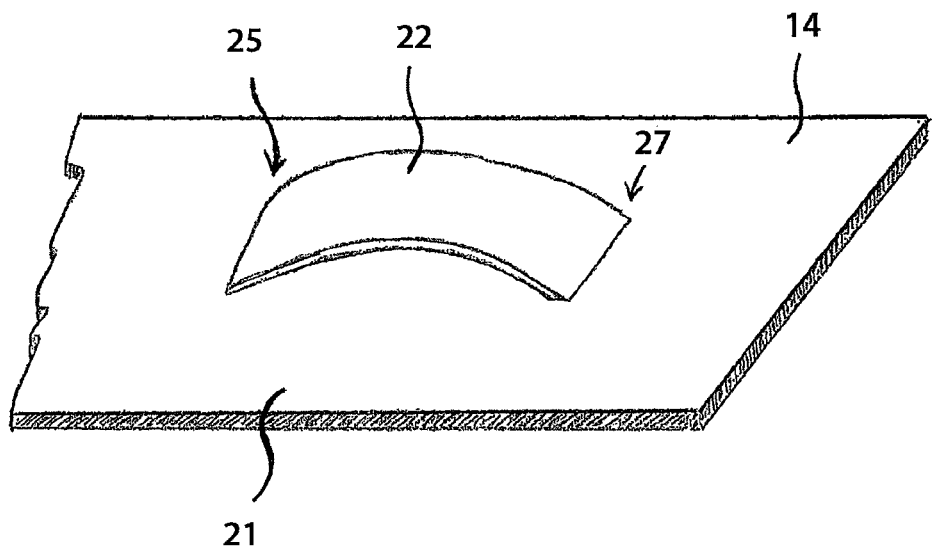
FIG. 14A is a perspective view of an eighth embodiment of the measurement system in which two opposite ends of an upper layer are attached to a stretchable base layer prior to tension being applied.
Figure 14B:
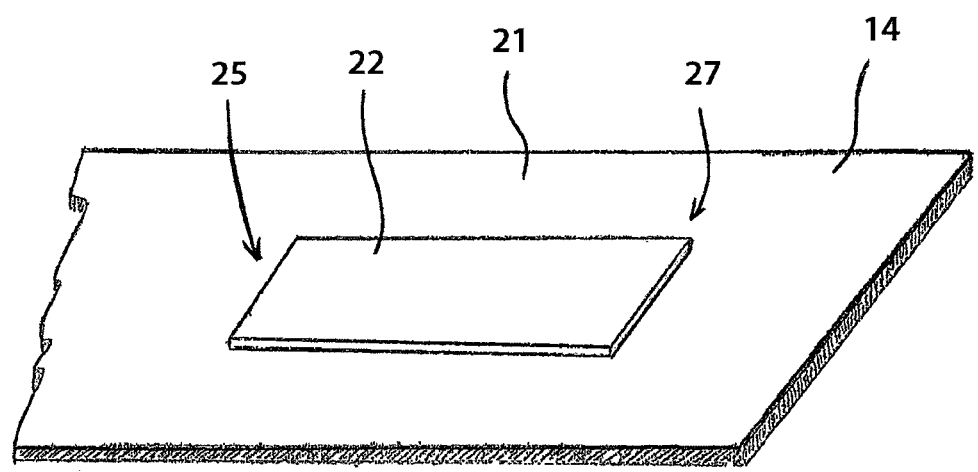
FIG. 14B is a perspective view corresponding to FIG. 13A, after tension has been applied showing the upper layer pulled flat against the stretchable base layer.

An eight embodiment of the invention is seen in FIGS. 14A and 14B in which the ends 25 and 27 of upper layer 22 are attached to stretchable base layer 21. As the base layer is stretched, upper layer 22 will eventually be pulled taught (FIG. 14A) against the base layer, thereby limiting or preventing further stretching.

What is claimed is:

1. A two-layer compression measurement system, comprising:
   (a) a stretchable continuous base layer having indicia thereon; and
   (b) an upper layer attached at two spaced-apart locations on top of the stretchable continuous base layer, thereby limiting the stretching in the stretchable continuous base layer underneath the upper layer between the two spaced-apart locations when the upper layer has been pulled taut.

2. The system of claim 1, wherein the upper layer comprises a first portion and a second portion attached end-to-end, the first and second portions having different stiffnesses, and wherein the first portion of the upper layer is attached to a first location of the stretchable base layer, and wherein the second portion of the upper layer is attached to a second location of the stretchable base layer.

3. The system of claim 2, wherein the first portion of the upper layer permits external viewing of the indicia therethrough.

4. The system of claim 3, wherein the first or second portion of the upper layer has a window for external viewing of the indicia.

5. The system of claim 3, wherein the first or second portion of the upper layer is transparent or translucent and the second portion of the upper layer is opaque.

6. The system of claim 3, wherein the indicia of the base layer further comprises a plurality of indicia, and wherein different indicia are viewable through the first or second portion of the upper layer depending upon an amount of stretch of the base layer.

7. The system of claim 6, wherein different indicia are viewable at different pre-determined compression levels including 20 mm Hg, 30 mm Hg, or 40 mm Hg.

8. The system of claim 3, wherein the indicia are positioned under the second portion of the upper layer and are not externally visible before the system has been stretched to a predetermined tension, and wherein the indicia are positioned under the first portion of the upper layer and are externally visible after the system has been stretched to the predetermined tension.

9. The system of claim 2, wherein the first portion of the upper layer is inelastic and the second portion of the upper layer is elastic.

10. The system of claim 2, wherein the first and second portions of the upper layer stretch together as the stretchable base layer stretches underneath.

11. The system of claim 2, wherein the location of attachment the first and second locations is adjustable such that the first and second portions can be aligned with the indicia on the stretchable base layer.

12. The system of claim 2, wherein the upper layer is rigidly attached to the stretchable base layer at first or second locations and releasably attached to the stretchable base layer at the other of the first or second locations.

13. The system of claim 12, wherein a length of the upper layer is adjustable such that the first or second locations of attachment can be aligned with the indicia on the upper layer.

14. The system of claim 13, wherein the length of the upper layer is adjustable by cutting the upper layer corresponding to different indicia.

15. A method of measuring compression of a compression garment for compression therapy, the method comprising:
   assembling the compression garment for wrapping around a limb, the garment comprising a body with a plurality of interlocking bands extending therefrom;
   positioning a two-layer compression measurement system on at least one of the interlocking bands, the measurement system operable to accurately measure an inwardly applied compression force to the limb resulting from a tension level in the at least one of the interlocking bands,
   the system comprising: a stretchable continuous base layer having indicia thereon; and an upper layer attached on top of the stretchable continuous base layer at two spaced apart locations, thereby limiting stretching in the stretchable continuous base layer underneath the upper layer when the upper layer has been pulled taut;
   externally viewing the indicia of the stretchable continuous base layer, the indicia of the stretchable layer accurately show the tension level; and
   correlating the indicia with the inwardly applied compression force.

16. The method of claim 15, further comprising: wrapping and affixing the garment around the limb.

17. The method of claim 16, further comprising: externally viewing the indicia of the stretchable continuous base layer through the first portion of the upper layer.

18. The method of claim 17, further comprising:
   positioning the indicia underneath the second portion of the upper layer such that the indicia of the stretchable continuous base layer are not externally visible before the measurement system has been stretched; and
   positioning the indicia under the first portion of the upper layer such that the indicia of the stretchable continuous base layer are externally visible after the measurement system has been stretched.

19. The method of claim 15, further comprising: attaching first and second portions of the upper layer end-to-end to the stretchable continuous base layer, each of the portions having different stiffnesses, wherein the first portion is attached to the stretchable continuous base layer at a first location of the stretchable continuous base layer and the second portion is attached to a second location of the stretchable continuous base layer.

20. The method of claim 19, further comprising: externally viewing different indicia of the stretchable continuous base layer through the first portion at different pre-determined compression levels.

* * * * *